United States Patent
Vandamme

(10) Patent No.: US 6,416,781 B1
(45) Date of Patent: *Jul. 9, 2002

(54) DEVICE FOR RELEASING WITH DELAYED EFFECT AN ACTIVE SUBSTANCE, IN PARTICULAR VETERINARY

(75) Inventor: M. Thierry Vandamme, Strasbourg-Cronenbourg (FR)

(73) Assignee: Virbac S.A., Carros (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/284,838
(22) PCT Filed: Oct. 20, 1997
(86) PCT No.: PCT/FR97/01880
   § 371 (c)(1),
   (2), (4) Date: Apr. 21, 1999
(87) PCT Pub. No.: WO98/17259
   PCT Pub. Date: Apr. 30, 1998

(30) Foreign Application Priority Data

Oct. 21, 1996 (FR) .............................................. 96 12761

(51) Int. Cl.⁷ ................................................. A61K 9/52
(52) U.S. Cl. ....................... 424/438; 424/454; 424/457; 604/95.04
(58) Field of Search ................................. 424/438, 404, 424/413, 451, 454, 457; 604/95.04, 516, 518

(56) References Cited

U.S. PATENT DOCUMENTS

| | | | | |
|---|---|---|---|---|
| 4,308,250 A | * | 12/1981 | Griffin et al. | 424/438 |
| 4,326,522 A | * | 4/1982 | Guerrero et al. | 424/438 |
| 4,381,780 A | * | 5/1983 | Holloway | 604/892 |
| 4,578,363 A | * | 3/1986 | Whitehead | 424/438 |
| 5,501,857 A | * | 3/1996 | Zimmer | 424/438 |
| 5,720,972 A | * | 2/1998 | Munday | 424/438 |
| 5,731,001 A | * | 3/1998 | Magruder et al. | 424/473 |
| 5,840,074 A | * | 11/1998 | Ayer et al. | 604/892.1 |
| 5,869,083 A | * | 2/1999 | Porter | 424/438 |

FOREIGN PATENT DOCUMENTS

| | | | |
|---|---|---|---|
| AU | 0449029 | * | 3/1972 |
| EP | 0164241 | * | 12/1985 |
| EP | 0164927 | * | 12/1985 |
| WO | WO 86/00519 | | 1/1986 |

OTHER PUBLICATIONS

US 4,927,419, 05/1990, Scully (withdrawn)

* cited by examiner

Primary Examiner—Neil S. Levy
(74) Attorney, Agent, or Firm—Young & Thompson

(57) ABSTRACT

A device for dispensing an active substance to be used in a biological medium, in particular in the rumen of an animal, includes a sealed receptacle for containing the substance, and having at least one opening; a closure for provisionally closing the opening of the receptacle, the closure being maintained closed by at least one biodegradable element such that subsequent to the biological degradation of the element, the closure completely releases the opening.

6 Claims, 7 Drawing Sheets

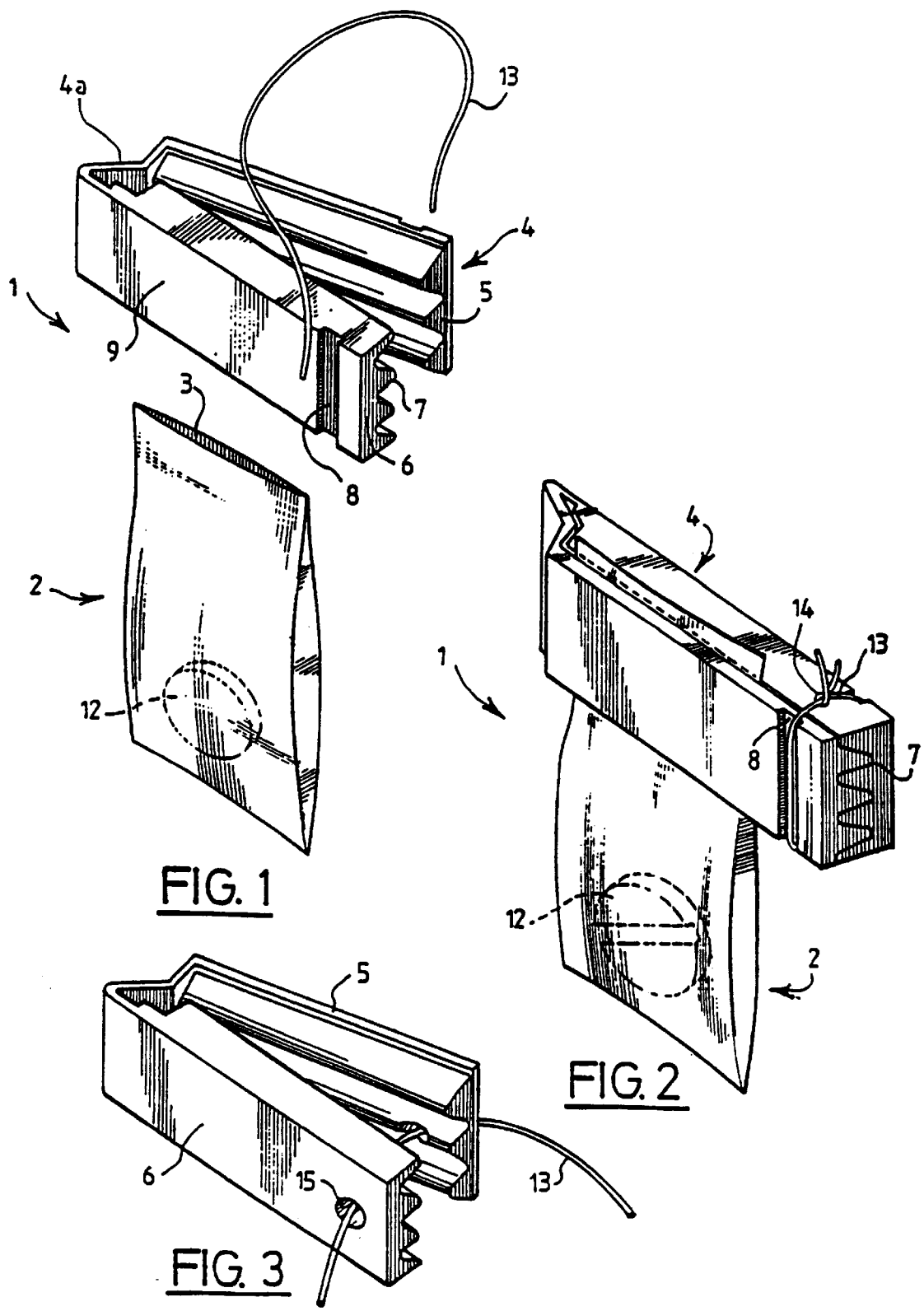

DEVICE FOR RELEASING WITH DELAYED EFFECT AN ACTIVE SUBSTANCE, IN PARTICULAR VETERINARY

This application is a 371 of PCT/FR97/01880 filed Oct. 20, 1997.

BACKGROUND OF THE INVENTION

The invention relates to a device for the delayed release of an active substance, especially a veterinary active substance.

DESCRIPTION OF THE RELATED ART

In the past fifteen years, much research has been carried out in veterinary pharmacy in order to optimize the release of medicinal products in domestic rearing animals or pets.

One of the main axes of research is directed towards developing anthelmintic compounds intended for the treatment of the verminoses of ruminants (bovines, goats, etc.). As regards the oral route, the most common formulations involve medicinal premixes or granules containing anthelmintic agents. More sophisticated formulations have also been designed for the oral route. These allow release of the active principle over a longer period of time and thereby avoid the need to regularly retreat the animals and to seek them out in the pasture in order to administer treatment. These devices with sustained release of active principle (also known as intraruminal diffusers or boli) allow release of the active principle by diffusion across a matrix excipient by erosion of one of the components constituting the device, by the action of an electronic system which allows programmed release over time, or alternatively by osmotic pressure.

These devices are maintained in the rumen of the ruminants either by means of the density of the device or its specific geometry which prevents regurgitation of the bolus during rumination.

However, on account of the constraints imposed by the size of the device which needs to be administered and the daily amount of product which needs to be released in order to obtain a pharmacological effect, one of the major problems lies in the fact that the active principle is released over an insufficient period, 140–150 days at most, with the amount of active principle released not increasing during the season in pasture, or even decreasing over time.

In addition, another drawback is that the active principle is essentially released during the first months in pasture, when the fields contain a relatively low number of worms and eggs, while the digestive tract and the lungs of the animals contain few worms or larvae at the start of the season in pasture. As a result, the animals generally show no infestation or any clinical signs due to verminoses during this period.

Furthermore, the immediate release of the active principle when the animals are placed in pasture at an early stage compromises the release of this active principle at a stage at which it would be necessary, i.e. in July and August.

Early release of the active principle also has the drawback of avoiding contact between the host and the infesting agent at a stage when this contact would allow the ruminant to acquire immune protection against these parasites.

A need thus exists for a device which would, on the one hand, allow a lag phase after ingestion of the device by the animal, before any release of active principle at the moment when the animals are placed in pasture, and which would, on the other hand, ensure a release of an active agent, in particular an anthelmintic agent, continuously or preferably in waves, in an amount increasing as a function of time during the months of July and August.

SUMMARY OF THE INVENTION

So as to satisfy such a need, the subject of the invention is a device for distributing an active substance, this device being intended to be used in a biological medium, in particular the rumen of an animal, comprising:

a leakproof container intended to contain the said substance, the said container comprising at least one opening;

a means for temporary closure of the opening of the said container, the said closure means being held closed by at least one biodegradable component, such that, after the said component has biodegraded, the closure means completely frees the said opening.

In a first embodiment, the container is a flexible leakproof sachet or a leakproof sachet with a certain amount of rigidity and which can be rolled up and unrolled. Any nonbiodegradable leakproof material may be suitable. Mention may be made of a nonbiodegradable polymer, in particular a polypropylene, polyester, polyvinyl, etc.

The closure means advantageously includes a member formed of two components which are applied one on top of the other.

These two components can be held together at each of their ends by the biodegradable component. They can also be linked together by a portion forming a hinge and held together at only one end by the said biodegradable component.

These two components preferably comprise complementary longitudinal grooves on their inner face, such that, when the two components are applied one on top of the other, the grooves interlock and ensure the total leaktightness of the closure means.

The closure means advantageously comprises a clip, which is normally open, and is held closed by means of the biodegradable component, the said clip preferably having arms comprising interlocking grooves.

In a second embodiment, the container is formed of a rigid cup of cylindrical shape, closed at one of its ends and open at its other end, and the means for temporary closure of the said open end comprises a disk pierced with a central orifice, a stopper whose shape matches that of this central orifice and which is held on the said central orifice by the biodegradable component supported by a ring, and by a collar intended to be fixed onto the cup in order to keep the disk and the ring applied against the open end of the said cup.

In a third embodiment, the receptacle is formed of a cylinder comprising a ballasting component at one of its ends and a stopper provided with perforations at these [sic] other end, and this cylinder comprises several superposed compartments each containing an active substance, the said compartments being interconnected and each being closed off by the said temporary closure means.

Each compartment is formed of a cartridge provided with outer screw threading at one of its ends and inner screw threading at its other end.

In this embodiment, the means for temporary closure of each compartment comprises a disk pierced with a central orifice, a stopper whose shape matches that of this central orifice and which is held on the said central orifice by the biodegradable component supported by a ring applied onto the said disk by the cartridge of the adjacent compartment.

In a fourth embodiment, the receptacle is formed of an envelope of elongate shape made of leakproof material which is not biologically degradable, the receptacle comprising an opening at at least one of its ends and containing a matrix formed of a resin in which particles of a high-density material and particles of the said active substance are distributed, the said opening being held closed by the said biodegradable component.

The envelope comprises an opening at each of its ends and the matrix comprises a passage extending over the entire length of the said matrix and aligned in the axis of the said openings, each of these openings being closed off by a stopper made of nonbiodegradable material and the said stoppers being linked together by the said biodegradable component.

In a fifth embodiment, the receptacle is formed of a cylindrical container comprising two half-shells linked together at one of their ends by a portion forming a hinge and at its other end by the said biodegradable component in order to keep the container temporarily closed.

The half-shells are advantageously designed to contain a delayed-release form of an active principle of the type comprising a matrix in which an active principle is dispersed and a central hollow being provided in the said matrix in order to allow a graded release of the active principle based on the differences in migration path of the active principle from the matrix to the central hollow.

The biodegradable component advantageously consists of a thread or a strip made of a biologically degradable polymer.

Any biodegradable polymer material is suitable. Mention may be made of polyglycolic acid (PGA), polylactic acid (PLA) or a copolymer of polyglycolic acid and of polylactic acid (PLGA), poly(ε-caprolactone) (PCL), poly(p-dioxanone), polyanhydrides, polyorthoesters, etc.

In one preferred embodiment of the invention, the biodegradable component consists of a surgical suture thread, in particular a single-filament or braided surgical suture thread.

Threads of this type which may be suitable are, in particular, polyamides, such as those described in U.S. Pat. No. 5,068,220, polyglycolic acid polymers, for example the one sold under the brand name Vicryl®; a copolymer of glycolic acid and of lactic acid, for example the one sold under the brand name Dexon®; a copolymer of trimethyl carbonate and of glycolic acid, for example the one sold under the brand name Maxon®; a poly(p-dioxanone), for example the one sold under the brand name PDS II®, an ε-caprolactone/glycolic acid block copolymer, for example the one sold under the brand name Monocryl®. The diameter of the thread or strip is variable and depends on the size of the device, the nature of the material used and the time after which its degradation is desired.

A person skilled in the art is capable of determining the thickness of this thread or strip, by means of routine calculations. Preferred suture thread sizes correspond to the numbers: 0, 1/0 and 2/0.

Closure of the strip or suture thread is ensured by maintaining tension on the ends of the strip or thread, by any suitable means, in particular by means of a knot or any external device for holding together the free ends of the thread or strip, such as adhesive, wax, a non-degradable polymer, a circlip, etc.

A bioresorbable screw made of a material which is resorbed by hydrolysis, such as a high molecular weight polymer of polylactic acid or polycaprolactone type, is also advantageously used.

A screw of this type is used in maxillofacial surgery and is sold under the name Phusiline®.

The biologically active substance advantageously consists of a medicinal product, in particular an anthelmintic agent, a growth promoter, etc., the device being intended in this case to be introduced into the stomach of a ruminant.

When the device is a flexible sachet, in particular, and when the suture thread has lost its mechanical properties, the release of the active substance can be facilitated by formulating the active principle in an effervescent pharmaceutical form or by adding an effervescent mixture with no pharmacological properties into the sachet along with the diffuser. In this case, the mixture can consist of citric acid and sodium bicarbonate, or other mixtures whose hydration produces a gas.

By dilating the flexible sachet, this gas facilitates the release of the active substance into the surrounding biological medium.

In order to avoid regurgitation phenomena, the device according to the invention, in particular in the form of the first embodiment of the invention, can be inserted in a bag which is provided with perforations or which allows easy diffusion of the active principle, or the sachet of the device will contain either a rolled-up sheet which, after unrolling, will prevent regurgitation of the device, or will be made more dense by the addition of a component for increasing the density.

Advantageously, the device then comprises a flexible or deformable sachet containing a support sheet in which an active principle is dispersed, the said support sheet being designed so as to be able to be arranged positively, by deformation, in a first rolled-up form and to take a second form in the rumen, the device being held in the rumen by virtue of this second form.

A subject of the invention is also a device as described for the first embodiment of the invention, comprising a flexible or deformable sachet containing a support sheet of the abovementioned type, the sachet and the support sheet being in a rolled-up form with the closure means located inside the roll, and the assembly being held in this rolled-up form by a positive deformation means which can be rapidly eliminated in the rumen.

The perforated sheet or sheet provided with perforations can also be rolled up around the device and the assembly included in a bag as described above.

Systems of this type in the form of a matrix capable of rolling up and unrolling once in the rumen of an animal are described in EP 334,516, U.S. Pat. No. 3,844,285 and EP 10,967.

The regurgitation phenomena can also be avoided by providing the device of the invention, in particular in the second, third and fourth embodiments of the invention, in an elongated cylindrical form provided with a ballasting component.

A subject of the invention is also a system for distributing one or more active substances, which is intended to be used in a biological medium, in particular the rumen of an animal, this system comprising at least two devices arranged one inside another, each container containing, optionally besides the said active substance, at least one other similar container, or each container being contiguous with the others.

In a first embodiment of the multi-container system of the invention, the system comprises a first outer device as described above in relation to the first embodiment of the invention, preferably containing an active substance and in turn comprising at least one other similar device containing a biologically active substance, this substance preferably being different from the one contained in the outer device or the device(s) arranged in the outer device. This system thus allows the release of biologically active substances of different nature, in particular of the substances which are incompatible in terms of chemical and/or physical stability or which are pharmacologically incompatible.

In a second embodiment of the multi-container system, the devices are organized in a nesting arrangement. In other words, the system comprises a first outer device containing, besides an active substance, a device of smaller size which contains, besides a second active substance, a third device smaller than the second device, and so on.

One or other of the systems described above can be designed so as to provide a sequential release as a function of the pharmacological, chemical and physical properties of several different active principles.

The active substances can be of different nature, or of the same nature and of different dosages. It is thus possible to provide a system of devices arranged one inside another in a nesting manner, in which the containers for the respective devices contain the same active substance, but at increasing doses, in going from the outermost system to the innermost system. In this manner, release of the biological substance will be obtained over time, such that, when this is an anthelmintic substance, the maximum dose will be released at a chosen moment, for example at the end of the season in pasture, or alternatively the release of active principles in different physical forms, for example a liquid active principle and another solid.

Nonlimiting examples of active principles with pharmacological activity which can be administered by means of a device and/or a system according to the invention are anthelmintic agents such as ivermectin, morantel tartrate, levamisole hydrochloride, oxfendazole, etc., trematicides, in particular rafoxanide, antibiotics and vaccines.

BRIEF DESCRIPTION OF THE DRAWINGS

The invention will be described in greater detail in the description which follows, for which reference will be made to the attached figures in which:

FIG. 1 represents an exploded perspective view of a first embodiment of a device according to the invention representing a container and its closure means;

FIG. 2 represents a perspective view of the container according to the first embodiment of the invention, held closed by means of a clip;

FIG. 3 represents a variant of the mode of closure of the clip in the device according to the first embodiment of the invention;

DESCRIPTION OF THE PREFERRED EMBODIMENTS

Figure 4:
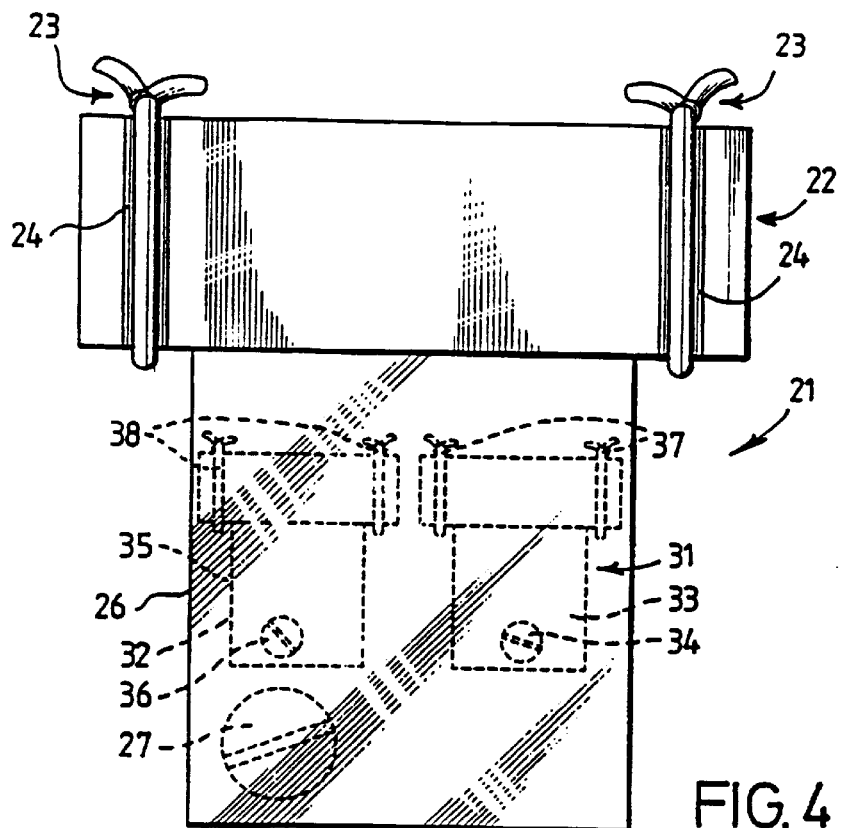
FIG. 4 represents a system composed of several devices according to the first embodiment of the invention, arranged one inside another.

The device 1 represented in FIG. 1 comprises a container 2 formed of a flexible leakproof sachet, three sides of which are welded, the fourth side 3 being held open.

The device also comprises a means for temporary closure of the open end 3 of the sachet 2. In this embodiment, this closure means consists of a clip 4 comprising two arms 5 and 6 linked at one of their ends by a linking portion 4a forming a hinge to hold the arms 5 and 6 of the clip in the open position in the absence of an external force.

Each arm 5 and 6 comprises longitudinal grooves 7 on its inner face.

A channel 8 extends over the outer faces 9 of the said arms.

The open end 3 of the flexible leakproof sachet 2 in which the active principle, in this case a tablet 12, has been placed, is placed between the open arms 5, 6 of the clip 4. These arms are then squeezed together as represented in FIG. 2, the grooves 7 interlocking, and held in this configuration by means of a biodegradable suture thread 13 located in the channel 8, the two ends of which are linked by means of a knot 14.

In this form, or after introduction into a perforated bag comprising an unrollable rolled-up sheet as described above, the device is introduced into the rumen of a bovine in a known manner, with the aid of a pistol commonly used for introducing boli into the digestive tract of a ruminant. The device can also be rolled up on itself, as described later.

On contact with the gastric juice in the rumen, the biodegradable suture thread 13 degrades gradually until it is broken, promoted by the tension exerted on the arms 5, 6 of the clip 4, at the desired moment of release of the active principle.

This tension exerted on the arms of the clip can also be increased by applying a spring system, not represented, between the arms 5, 6 of the clip 4.

FIG. 3 represents a variant of the mode of fixing of the suture thread 13 onto the arms 5, 6 of the clip 4. In this embodiment, the arms 5, 6 each contain a hole 15. The biodegradable suture thread 13 is introduced into these holes and its ends are linked by any means, in particular a knot.

Also as a variant, the arms of the clip can comprise a ring at their end, in which case they are held together by means of a thread passing through the two rings, the ends of the thread being linked together by a suitable means, for example a knot.

The durations after which a device as described above releases the active principle it contains will be given below. The threads used are all No. 2/0 threads, with a diameter of between 0.30 and 0.35 mm.

| Nature of the No. 2/0 suture thread | Time after which the substance is released |
| --- | --- |
| Cat gut | 7–10 days |
| Chromium plated cat gut | 21–28 days |

-continued

| Nature of the No. 2/0 suture thread | Time after which the substance is released |
|---|---|
| Vicryl Rapide | 12 days |
| Monocryl ® | 21 days |
| Vicryl ® | 30 days |
| PDS II | 60 days |

FIG. 4 represents a distribution system according to the invention comprising a first device 21 as described above, but with a closure member 22 comprising two components which fit together in a leak-tight manner, the two components being held together at each of their ends by means of a biodegradable thread 23 inserted into a channel 24, and the two ends of which are linked together by means of a biodegradable suture thread 23 as described above.

This first outer device comprises a flexible sachet 26 containing an anthelmintic active principle in the form of a tablet 27, as well as two other identical devices 31, 32 which are smaller than the first outer device 21. The flexible sachet 33 of the device 31 comprises, for example, a tablet 34 of an anthelmintic active principle and the flexible sachet 35 of the device 32, a gelatin capsule 36 containing a vaccine the form of a lyophilizate, these two compounds showing pharmacological and possibly chemical incompatibility.

In another application, one of the devices can contain an acidic anthelmintic agent, for example levamisole hydrochloride, or a strongly basic anthelmintic agent; another device in this case containing, for example, an antibiotic which can be decomposed in acidic or strongly basic medium.

In yet another application, one of the devices can contain an active principle in the form of an anion, and another device can contain an active principle in the form of a cation, so as to avoid the formation of a pair of ions.

By virtue of this embodiment, a simultaneous or staggered release can be obtained, depending on the nature and/or thickness of the biodegradable threads 37, 38 on the devices 31, 32 during the summer months when the need for an anthelmintic and trematicidal treatment will be greatest.

Figure 5:
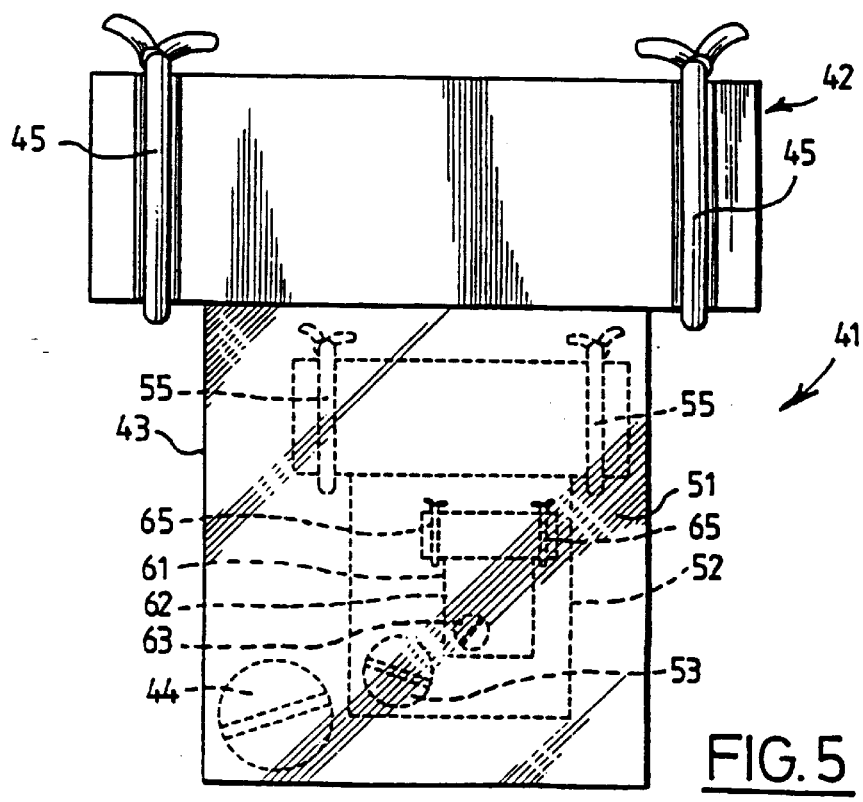
FIG. 5 represents a system composed of several devices according to the first embodiment of the invention, organized in a nesting arrangement.

FIG. 5 represents another distribution system according to the invention.

It comprises a first outer device 41, as described in FIG. 1 or 2, with a closure member 42 identical to those in the devices of FIG. 4. The flexible sachet 43 of the device 41 contains a tablet 44 of an anthelmintic active principle at a first dose $x_1$ and another device 51, identical to the first but smaller than it in size. The flexible sachet 52 of this second device 51 contains a tablet 53 of the same anthelmintic active principle at a dose $x_2$, as well as a device 61 identical to the first two and even smaller in size than the second device 51, and the flexible sachet 62 of which contains a tablet 63 of the same active principle at a dose $X_3$.

The biodegradable threads 45, 55, 65 of the various "nesting" devices 41, 51, 61 are preferably designed so as to release their respective active principles in June, preferably at the end of June, July and August. The dose $x_1$ released in June is the lowest, the proliferation of the parasites being at its minimum, whereas the doses $x_2$ and $X_3$ are released at the end of July and the end of August and are suited to the increasing amounts of worms found in pastures at these periods, and also to the weight increase of the animal.

When the medicinal product is an anthelmintic agent, the threads are preferably designed to allow a first release of product one to two months after the animals have been placed in pasture (end of April-start of May) and the subsequent releases at intervals of 21 to 30 days, corresponding to the larval cycle.

Figure 6:
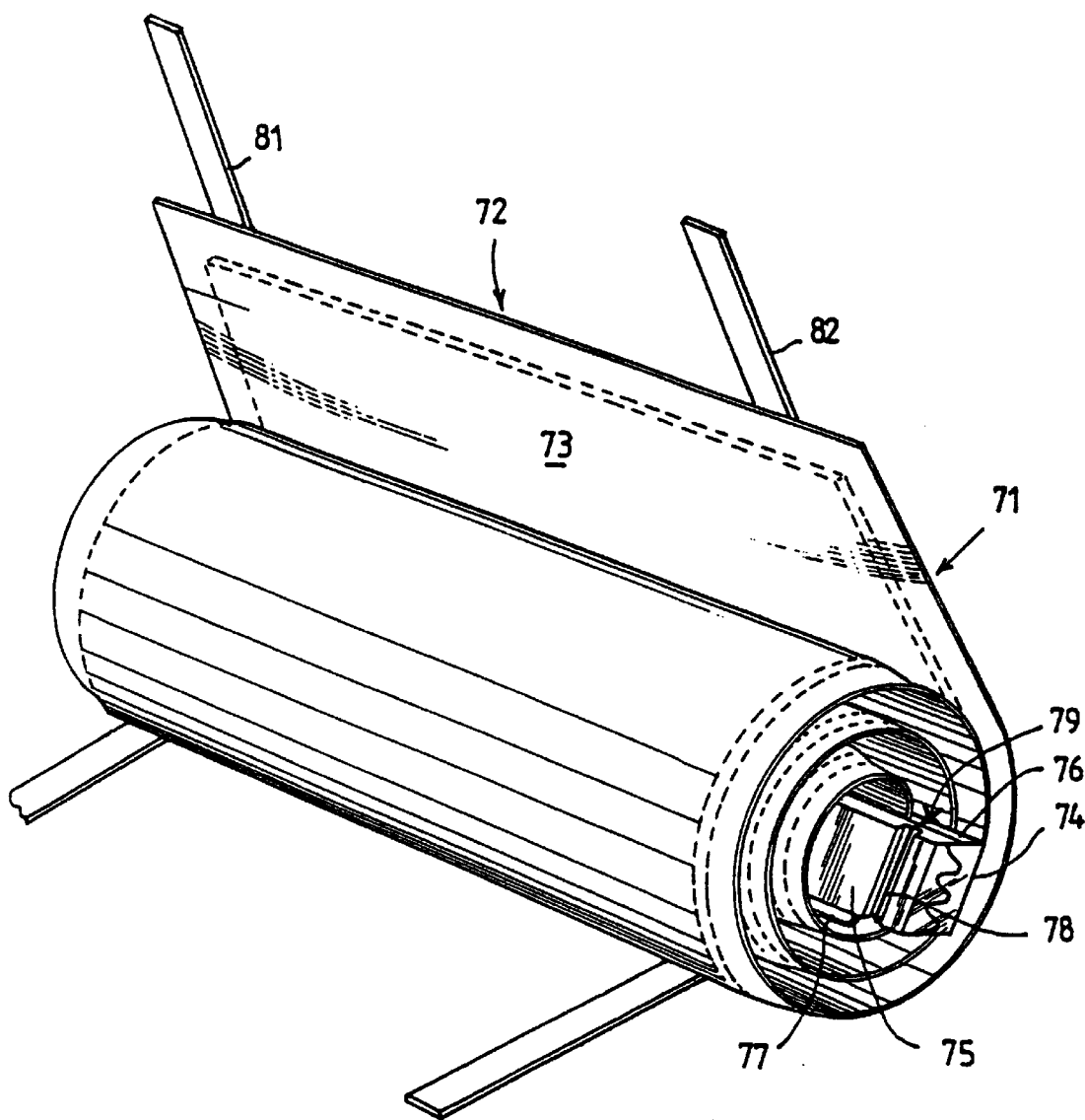
FIG. 6 represents a perspective view of a second embodiment of a device according to the invention, in a form which is particularly suitable for administration to a ruminant.

FIG. 6 represents a device according to the invention in a form which is particularly suitable for administration to a ruminant, in particular a bovine.

This device 71 comprises a deformable sachet 72 containing a support sheet 73 made of a water-insoluble polymer material, in which is dispersed a medicinal product. The support sheet is designed so as to be able to be positively arranged, by deformation, in a first rolled-up form.

As represented in FIG. 6, the dimensions of the support sheet 73 are slightly smaller than those of the deformable bag 72.

The device also comprises a clip 74 whose arms 75, and 76 grip the open end 77 of the deformable sachet 72 and are held together with the aid of a suture thread 78 closed with a knot 79.

In a first stage, the support sheet 73 in which the active principle is dispersed is introduced into the sachet 72 and the open end of the sachet is closed using the clip 74; the assembly is then arranged by positive deformation, for example by heating the support sheet to a temperature sufficient to soften the polymer but not to decompose the medicinal product, in the rolled-up form represented in FIG. 6, such that the clip 74 is inside the rolled-up form.

The assembly can be held in this position by an appropriate means, for example one or two strips of adhesive paper 81, 82 bearing a water-soluble adhesive or one or two strips of a water-soluble polymer, in particular gelatin.

After oral administration, the strips of paper become detached or the gelatin dissolves and the device unrolls, leaving its first form under the influence of the elasticity of the support sheet, and taking up a substantially flat second form by virtue of which the device is retained in the bovine's stomach.

The polymer support sheet in which the medicinal product is dispersed is, for example, of the type described in patent EP-010,967.

Figure 7:
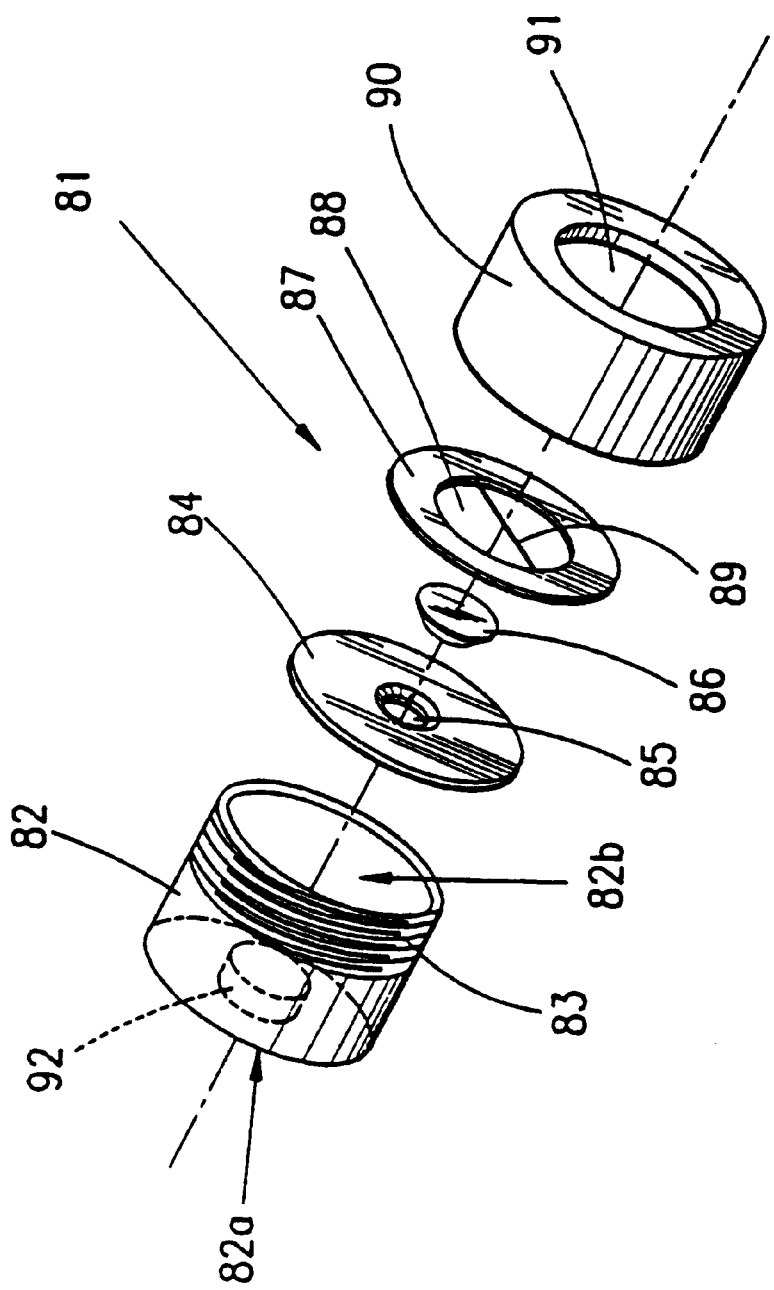
FIG. 7 represents an exploded perspective view of a device according to the invention representing a container and its closure means.

FIG. 7 represents a second embodiment of a distributor device according to the invention.

This device comprises a container denoted as a whole by the reference number 81 and formed of a rigid cup 82 of cylindrical shape, one end 82a of which is closed and the other end 82b of which is open.

The cup 82 comprises screw threading 83 at its open end 82b and on its outer face.

Moreover, the container 81 also comprises a means for temporary closure of the open opening 82b of the cup 82.

This temporary closure means consists of a thin disk 84 with an outside diameter substantially equal to that of the cup 82 and pierced with a central orifice 85, and preferably of frustoconical shape.

The top of the cone body delimited by the central orifice 85 faces into the cup 82.

The temporary closure means also comprises a stopper 86 whose shape matches that of the central orifice 85 of the disk 84, i.e. of frustoconical shape.

The temporary closure means also comprises a ring 87 whose outside diameter is substantially equal to the outside diameter of the cup 82. This ring 87 comprises a central bore 88 inside which is fixed the biodegradable component 89 which holds the stopper 86 in the central orifice 85 when the container 81 is closed, as will be seen later.

The biodegradable component 89 is preferably formed of a biodegradable thread whose ends are fixed to two diametrically opposite points of the bore 88 of the said ring 87.

Finally, the temporary closure means comprises a collar 90 provided with an orifice 91 at one of its ends and screw threading, not represented, on its inner face, which is intended to cooperate with the outer screw threading 83 of the cup 82.

The assembly formed of the disk 84, the stopper 86 and the ring 87 holding the said stopper 86 on the central orifice 85 is positioned on the open end 82b of the cup 82 and this assembly is held on the said open end 82b by the collar 90 which is screwed onto the cup 82.

A tablet 92 containing an active principle is placed in the cup 82, on which are successively placed the disk 84, the stopper 86, the ring 87 and the collar 90 which is screwed onto the cup 82.

The choice of the nature and size of the biodegradable thread 89 are determined by the duration after which the degradation of the said thread 89 and the release of the active principle by means of the tablet 92, are desired.

Following the movements of the medium in which it is placed, for example the animals movements, the stopper 86 then frees the orifice 85, into which the surrounding liquid medium penetrates, giving rise to the release therein of the active principle contained in the container 81.

The various components constituting this container 81 are made of a plastic or metal material.

Now, with reference to FIGS. 8 and 9, a third embodiment of the distributor device in accordance with the invention will be described.

Figure 8:
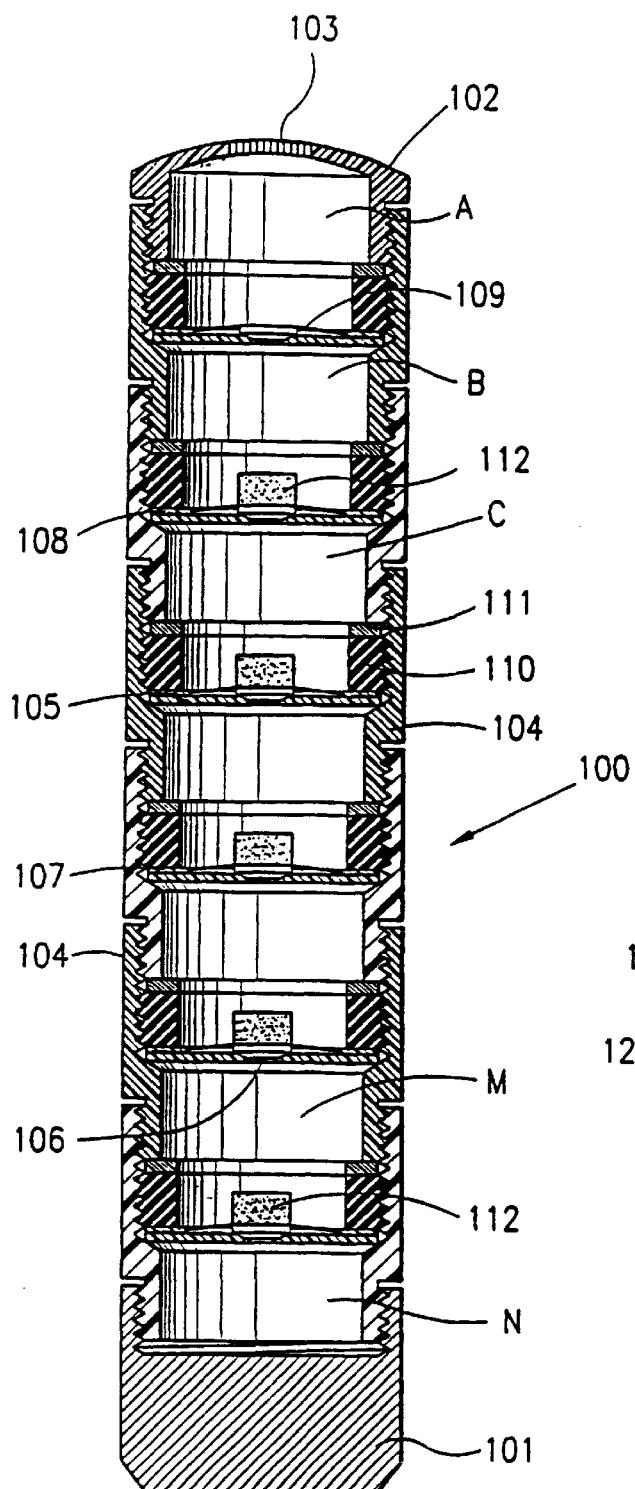
FIG. 8 represents a longitudinal view of a third embodiment of a device according to the invention.
Figure 9:
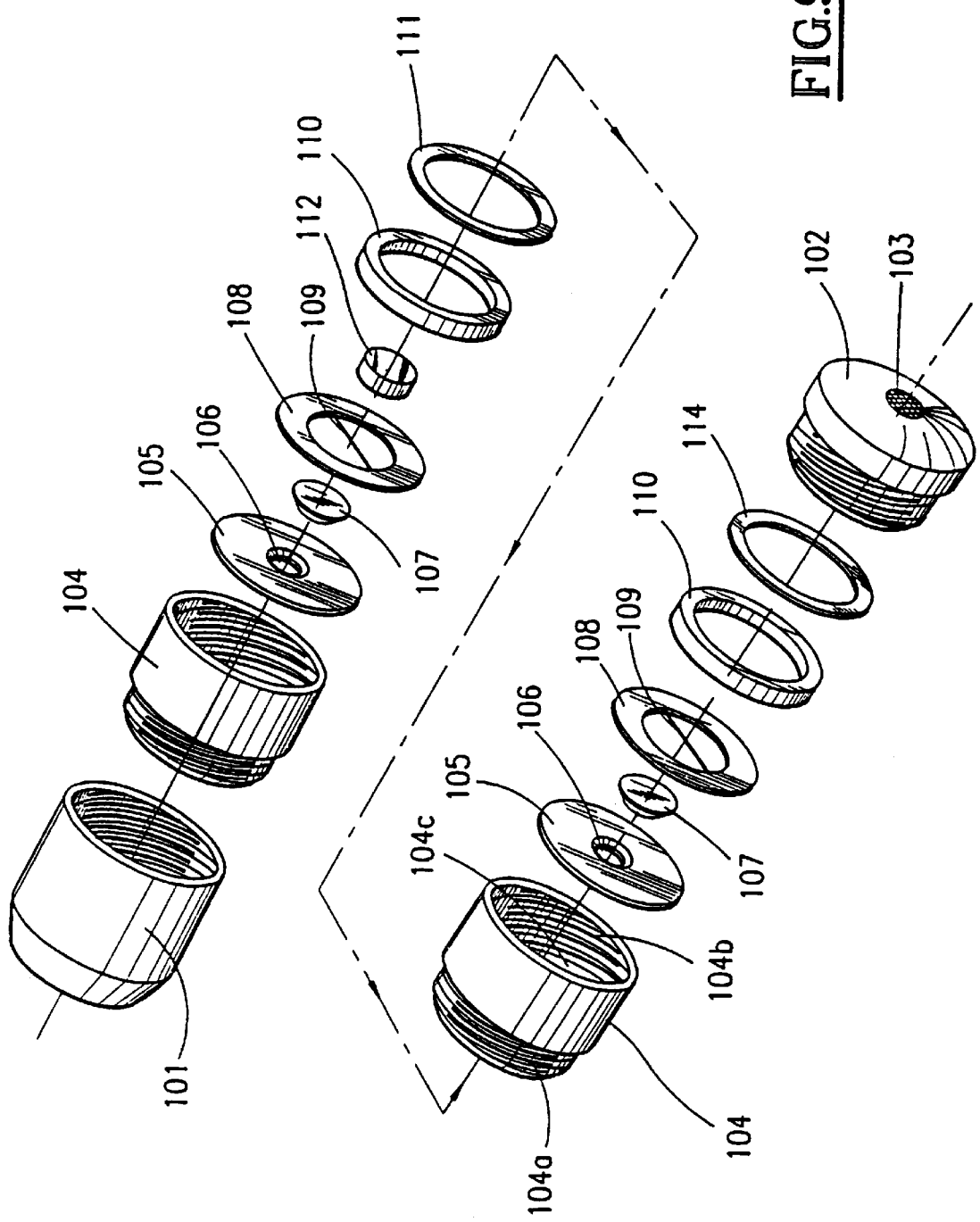
FIG. 9 represents an exploded perspective view of one part of the device according to the third embodiment.

As represented in FIG. 8, the container of the distributor device is formed of a cylinder denoted as a whole by the reference number 100, containing a ballasting component 101 at one of its ends and a stopper 102 provided with perforations 103 at its other end.

The free end of the ballasting component 101 is preferably in a frustoconical shape.

The cylinder 100 comprises several compartments, A, B, . . . N, respectively, which can each contain an active substance. These compartments A, B, . . . N, are interconnected and are each closed off by a temporary closure means. One compartment of the cylinder 100 will be described with reference more particularly to FIG. 9, the other compartments being identical.

Each compartment is formed of a cartridge 104 provided at one of its ends with outer screw threading 104a and at its other end with inner screw threading 104b.

The cartridge 104 comprises on the inside, substantially in its mid-section, an inner rim 104c intended to receive the temporary closure means of the corresponding compartment.

This means for temporary closure of each compartment comprises a disk 105 pierced with a central orifice 106, of frustoconical shape, and a stopper 107 whose shape matches that of the central orifice 106.

The temporary closure means also comprises a ring 108 comprising a biodegradable thread 109 intended to hold the stopper 107 in the orifice 106 of the corresponding disk 105.

The disk 105 and the ring 108 are held against the rim 104c of the corresponding cartridge 104 by the lower edge of the threaded end 104a of the adjacent cartridge 104.

A sealing joint 110 and a collar 111 are placed between the ring 108 and the lower edge of the threaded end 104a of the corresponding cartridge 104.

As represented in FIG. 8, the threaded end 104a of the cartridge 104 of the lower compartment N is intended to be screwed into the ballasting component 101 and the upper threaded end 104b of the cartridge 104 of the upper compartment A is intended to receive the stopper 102.

The various components comprising the cylinder 100 of the distributing container are preferably made of plastic or metal.

The perforations 103 in the lid 102 allow the passage of the biological liquid medium in which the release system is placed and these perforations 103 are small enough not to allow the passage of fibres or other solid elements which might be in the surrounding medium and which might harm the release of the active substance contained in each compartment.

Advantageously, the upper compartment A of the device contains no tablets containing an active principle, such that, where appropriate, the animal has the time to acquire a certain level of protective immunity before the number of parasitic worms becomes too large.

The liquid biological medium penetrates into the first compartment A via the perforations 103 and, at the end of the period envisaged, this biological medium degrades the biodegradable thread 109 of the said first compartment A so as to result in the release of the stopper 107 closing the orifice 106 which communicates with the second compartment B of the device.

The biological liquid in the surrounding medium can then penetrate into the next compartment B and bring about disintegration of the tablet 112 located inside this compartment B and result in the release of the active principle contained in this tablet 112 into the surrounding biological medium.

The successive opening of each compartment can take place at regular or irregular intervals depending on the nature and thickness of the biodegradable thread(s) 109.

Each compartment can contain the same active principle at identical or different doses, for example progressively increasing doses, or can contain active principles according to the desired pharmacological activity or the desired pharmacokinetics.

Figure 10:
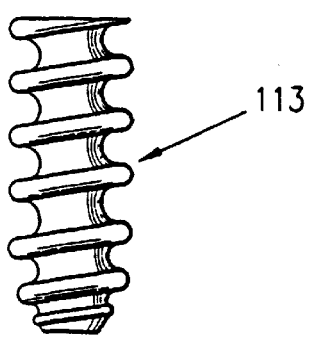
FIG. 10 represents a biodegradable component in the form of a biodegradable screw.

Instead of the biodegradable thread 109, each compartment can be closed off by a stopper in the form of a screw 113, as represented in FIG. 10.

Figure 11:
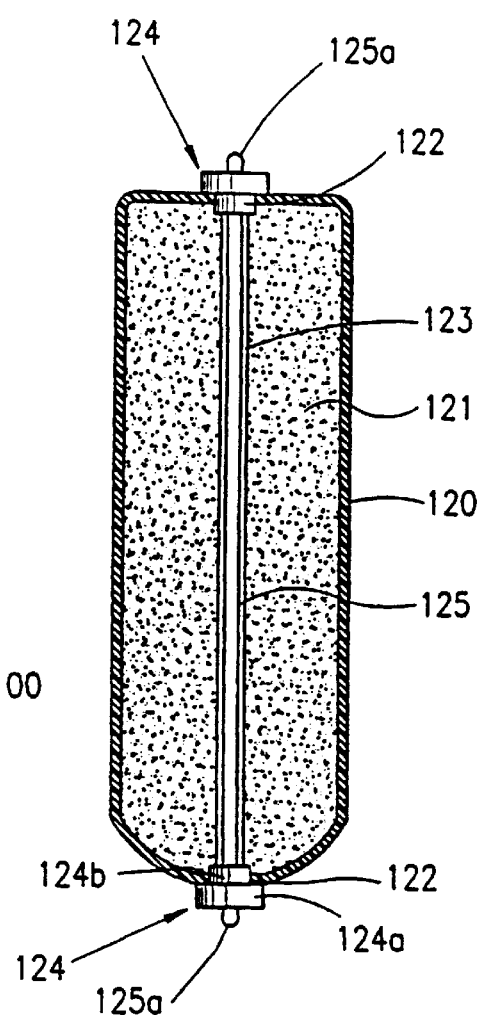
FIG. 11 represents a view in longitudinal cross section of a fourth embodiment of a device according to the invention.

FIG. 11 represents a fourth embodiment of the distributing device according to the invention.

In this embodiment, the container is formed of an elongate envelope 120 made of leakproof material which is not biologically degradable and comprises an opening at at least one of its ends.

The envelope 120 contains a matrix 121 whose shape matches that of the said envelope 120.

This matrix 121 is formed of a resin in which are distributed particles of a material of high density and particles of the active substance.

The opening of the envelope 120 is held closed by means of a biodegradable component.

The envelope 120 preferably comprises an opening 122 at each of its ends and the matrix 120 preferably comprises a passage 123 extending along the entire length of the said matrix 121 and arranged in the axis of the said openings 122.

As represented in FIG. 11, each opening 122 is temporarily closed by a stopper 124 comprising a first cylindrical part 124a whose diameter is slightly larger than the diameter of the opening 122, and a second cylindrical part 124b whose diameter is slightly smaller than the diameter of the opening 122. The second part 124b is designed to fit into the corresponding opening 122 and close it off temporarily.

The stoppers 124 are held in place in the openings 122 by the tension exerted by the biodegradable component, which, in this case, consists of a thread 125 in the form of a loop.

This biodegradable thread 125 extends over the entire length of the hollow 123 and crosses the stoppers 124 at two different points, forming a rounded end 125a which projects beyond each stopper 124 and is accessible for degradation by the surrounding biological medium.

The biodegradable thread 125 is designed to be broken at one or both of its rounded ends 125a, after a predetermined time, under the action of the surrounding biological liquid medium. The tension exerted by the thread 125 is then released and the stoppers 124 are released from the openings 122.

The biological liquid can then penetrate into the passage 123 made in the matrix 121 and the particles of active principle can be released at a rate which is a function of their distance from the central longitudinal axis of the passage 123.

In this embodiment, the stoppers 124 are made, for example, of rubber or silicone.

In one variant, not represented, of this embodiment, the biodegradable thread can form a loop around the outer contour of the envelope 120. For this, the biodegradable thread 123 links each stopper 124, passing through each one transversely.

In a second variant, not represented, of this embodiment, the envelope 120 comprises at least one opening 122 which is temporarily closed off by a biodegradable screw 113 as represented in FIG. 10. In this case, the corresponding orifice 122 comprises inner screw threading.

Figure 12:
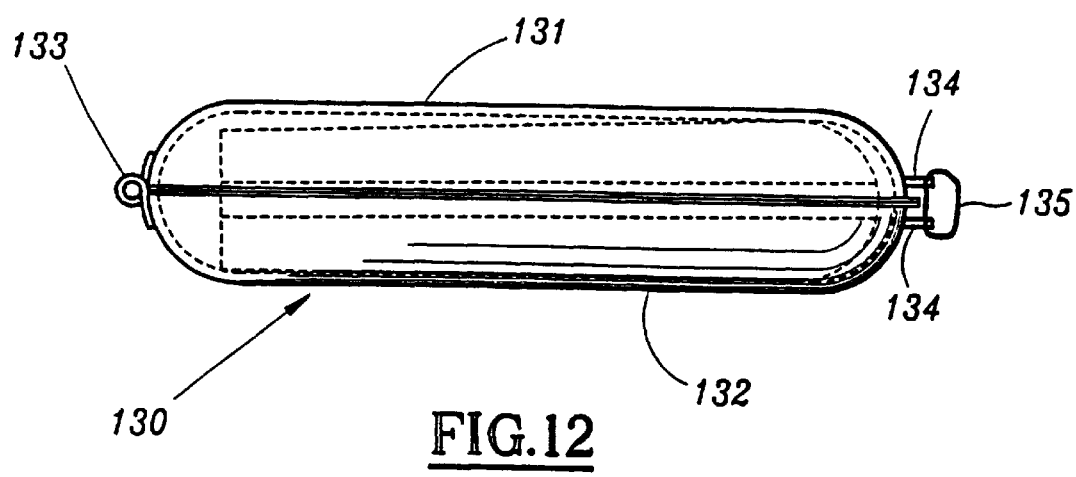
FIG. 12 represents a front view of a fifth embodiment of a device according to the invention, in the closed position.
Figure 13:
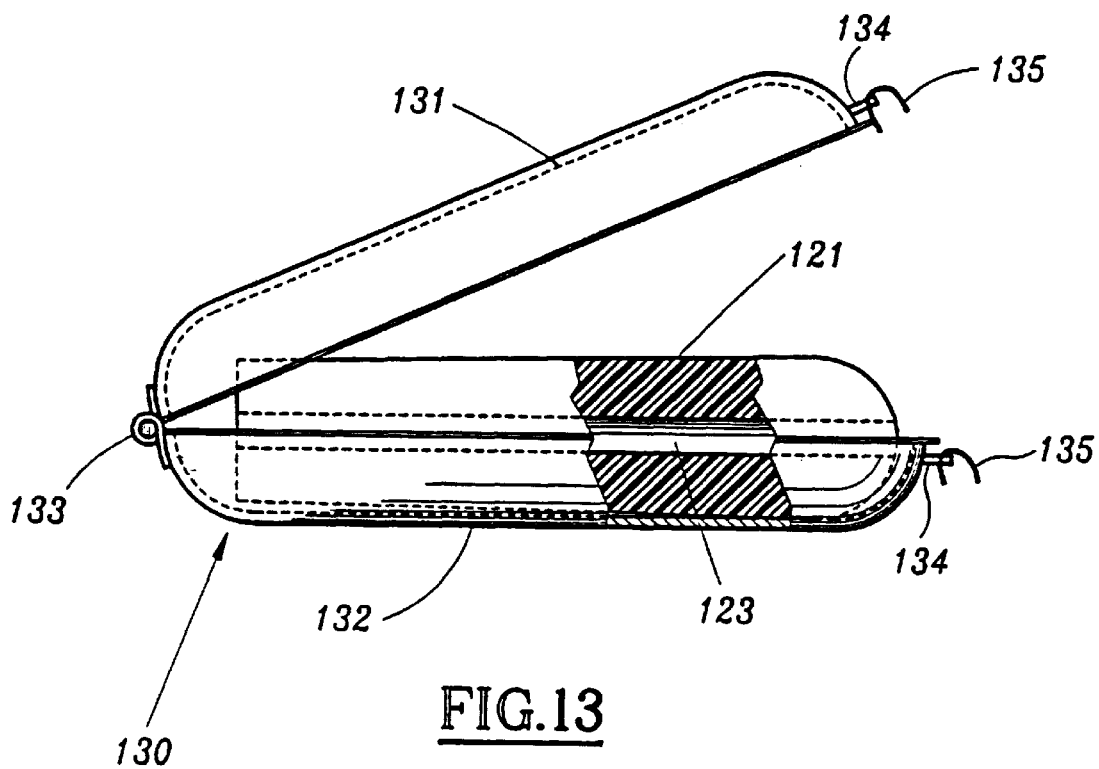
FIG. 13 represents a front view of the device according to the fifth embodiment, in the open position.

FIGS. 12 and 13 represent a fifth embodiment of the distributing device in accordance with the invention.

In this embodiment, the container is formed of a cylindrical envelope 130 comprising two half-shells 131 and 132 respectively.

The separation plane delimited by the two half-shells 131 and 132 extends along the longitudinal axis of the envelope 130.

The half-shells 131 and 132 are hinged at one of their ends by a portion 133 forming a hinge and each comprise an eyelet 134 at the end opposite the one comprising the portion 133.

The half-shells 131 and 132 are held in a closed position by means of a biodegradable thread 135 passing through the eyelets 134.

The envelope 130 contains a delay form, comprising a matrix in which is located an active principle, the matrix being designed for sustained release of the active principle.

Such a delay form can consist of the delay form 121 described in relation to FIG. 11.

The devices and systems according to the invention can be used in the rumen of ruminants as described above, in particular bovines, sheep and goats.

They can also serve for other types of use in which a programmed release or a release delayed over time, into a biological medium, of a substance such as a medicinal agent, a pesticide, a protein, a peptide, an enzyme, a nutrient or genetic material is desired. The biological medium can be an aquatic environment such as a river, a pond, an aquarium or a drinking trough.

The devices and systems according to the invention also have healthcare applications, in particular for the delayed release over time of disinfectants, bacteria, etc.

What is claimed is:

1. A device for distributing an active substance in an animal by oral administration, comprising:

plural dosages, each dosage comprising of an active substance for an animal;

a leakproof container containing the dosage, the leakproof container comprising at least one opening; and a closure means for temporary closure of each of the at least one opening of the leakproof container, the closure means being held closed, and under tension, by at least one biodegradable component comprising a thread or a strip, such that, after the component has biodegraded, the closure means completely frees the opening, the leakproof container further comprising a cylinder with a ballasting component at one end and a perforated stopper at another end, the cylinder comprising plural superimposed compartments, each compartment comprising one of the plural dosages, the plural compartments being interconnected and each of the compartments being closed off by one of the closure means.

2. A device according to claim 1, wherein, each compartment further comprising a cartridge provided with an outer screw threading at one end and an inner screw threading an another end.

3. A device according to claim 1, wherein, the closure means for each of the superimposed compartments comprises a disk pierced with a central orifice, and a stopper whose shape matches that of the central orifice, the stopper being held on the central orifice by the biodegradable component supported by a ring applied onto the disk by the cartridge of an adjacent compartment.

4. A device according to claim 1, wherein, the closure means comprises a member formed of two components which are applied one against the other.

5. A device according to claim 1, wherein, the two components being held together by the biodegradable component.

6. A device for distributing an active substance in an animal by oral administration, comprising:

plural dosages, each dosage comprising of an active substance for an animal;

a leakproof container containing the dosage, the leakproof container comprising at least one opening; and a closure means for temporary closure of each of the at least one opening of the leakproof container, the closure means being held closed, and under tension, by at least one biodegradable component comprising a thread or a strip, such that, after the component has biodegraded, the closure means completely frees the opening, the leakproof container further comprising a cylinder the cylinder comprising plural superimposed compartments, each compartment comprising one of the plural dosages, the plural compartments being interconnected and each of the compartments being closed off by one of the closure means.

* * * * *